United States Patent
Tanaka et al.

(10) Patent No.: US 6,705,312 B2
(45) Date of Patent: Mar. 16, 2004

(54) INHALATOR ATTACHMENT AND NEBULIZER EQUIPPED WITH SAME

(75) Inventors: Shinya Tanaka, Kyoto (JP); Takao Terada, Kyoto (JP)

(73) Assignee: Omron Corporation, Kyoto (JP)

( * ) Notice: Subject to any disclaimer, the term of this patent is extended or adjusted under 35 U.S.C. 154(b) by 0 days.

(21) Appl. No.: 10/227,377

(22) Filed: Aug. 22, 2002

(65) Prior Publication Data

US 2003/0062038 A1 Apr. 3, 2003

(30) Foreign Application Priority Data

Sep. 28, 2001 (JP) ........................................ 2001-301522

(51) Int. Cl.⁷ ............................................. A61M 11/00
(52) U.S. Cl. ............................ 128/200.14; 128/200.14; 128/200.16; 128/200.17
(58) Field of Search ........................ 128/200.14, 200.16, 128/200.17, 200.18, 200.21

(56) References Cited

U.S. PATENT DOCUMENTS

| | | | | |
|---|---|---|---|---|
| 2,622,593 A | * | 12/1952 | Peirano .................. | 128/200.18 |
| 3,291,122 A | * | 12/1966 | Engström et al. ....... | 128/200.16 |
| 3,490,697 A | * | 1/1970 | Best, Jr. .................. | 239/102.2 |
| 3,561,444 A | * | 2/1971 | Boucher ................ | 128/200.16 |
| 4,113,809 A | * | 9/1978 | Abair et al. ................... | 261/81 |
| 4,976,259 A | * | 12/1990 | Higson et al. ......... | 128/200.18 |
| 5,429,302 A | * | 7/1995 | Abbott ..................... | 239/102.2 |
| 5,435,282 A | * | 7/1995 | Haber et al. ........... | 128/200.16 |
| 5,511,539 A | * | 4/1996 | Lien ....................... | 128/200.21 |
| 5,551,416 A | * | 9/1996 | Stimpson et al. ....... | 128/200.16 |
| 5,727,541 A | * | 3/1998 | Rowland ............... | 128/200.14 |
| 5,908,158 A | * | 6/1999 | Cheiman ................. | 239/102.2 |
| 5,921,232 A | * | 7/1999 | Yokoi et al. ........... | 128/200.14 |
| 6,283,118 B1 | * | 9/2001 | Lu ......................... | 128/200.16 |
| 6,341,732 B1 | * | 1/2002 | Martin et al. ................... | 239/4 |

* cited by examiner

Primary Examiner—Aaron J. Lewis
(74) Attorney, Agent, or Firm—Beyer Weaver & Thomas LLP

(57) ABSTRACT

A nebulizer has a main body and an inhalator attachment which is detachably attached to the main body. The attachment has a tubular member including an receptacle. The tubular member has a medicament inlet for receiving nebulized medicament from the nebulizer, an inhalation opening which is opposite the medicament inlet and through which a patent inhales the nebulized medicament passed through the tubular member, and an air inlet through which air outside is introduced and passed through the tubular member. A brim member for guiding droplets of liquefied medicament and the user's saliva into the receptacle is formed partially around the medicament inlet. The air inlet is preferably formed by cutting the tubular member at the medicament inlet.

10 Claims, 5 Drawing Sheets

INHALATOR ATTACHMENT AND NEBULIZER EQUIPPED WITH SAME

BACKGROUND OF THE INVENTION

This invention relates to an attachment to an inhalator and a nebulizer equipped with such an attachment. More particularly, this invention relates to such an attachment for preventing droplets of liquid medicament and the user's saliva from dripping out.

An inhalator, or a nebulizer, is principally used for a therapeutic purpose. A medicament in a liquid form is nebulized by a nebulizer into a particle form and the patient, breathing in the nebulized medicament through the mouth or the nose, treats ailments in the bronchial tube, the nose cavity and the throat.

Nebulizers of different forms have been available, including the recently developed so-called ultrasonic nebulizers using a mesh. Such modem nebulizers are easily portable and capable of efficiently nebulizing a medicament. The nebulized medicament must be inhaled by the patient efficiently but there are patients who are not skilled in effectively inhaling nebulized medicament. Thus, various accessories and attachments have come to be used such as mouthpieces and masks.

A mouthpiece is a tubular inhalation attachment with one end part adapted to be inserted into the patient's mouth such that the nebulized medicament will be inhaled through the mouth. A mask is for covering both the patient's mouth and nose such that the nebulized medicament will be inhaled through both the mouth and the nose.

Inhalation attachments of either of these kinds are adapted to have one of its end parts connected to a nebulizer such that this end part will communicate with the medicament-emitting outlet opening of the nebulizer. The nebulized medicament emitted through this outlet opening generates an air flow inside the cylindrical body of the inhalation attachment. An air flow is also generated as the patient breathes in for inhaling the nebulized medicament. In order to maintain an appropriate air flow, an inhalator attachment is provided with an air intake opening for taking in air from outside. Without such an air intake opening, the air flow ceases to exist within the cylindrical body and it becomes impossible to inhale the medicament liquid.

It frequently happens with most inhalators that the nebulized medicament becomes attached to the inner wall of the cylindrical body and forms droplets which drip down on the inner surface and drop out of the air intake opening. If the patient is an infant, saliva may also start flowing out of the air intake opening. The droplets of medicament and the patient's saliva dripping out of the air intake opening may remain on the outer surface of the nebulizer or scatter around. It is not only unsightly and unpleasant to the patient as well as to persons around but also a hygienical problem to be addressed to.

In view of this problem, there have been attempts to provide a liquid storage space inside an inhalator attachment but the inhalator attachment becomes structurally complicated if so designed. Since such a liquid-storing space cannot be formed easily as a single component, the number of constituent parts increases and this affects the production cost adversely.

SUMMARY OF THE INVENTION

It is therefore an object of this invention to provide an improved inhalator attachment capable of maintaining a steady air flow inside a cylindrical body while preventing the droplets of medicament and the patient's saliva from dripping out.

It is another object of this invention to provide such an inhalator attachment that can be produced without increasing the production cost.

It is still another object of this invention to provide a nebulizer equipped with such an attachment.

An inhalator attachment to a nebulizer according to this invention may be characterized as comprising not only a tubular member having a medicament inlet for receiving nebulized medicament from the nebulizer, an inhalation opening which is opposite the medicament inlet and through which a patent inhales the nebulized medicament passed through the tubular member and an air inlet through which air outside is introduced to be passed through the tubular member but also a brim member for guiding liquid droplets on the tubular member into a receptacle. With an attachment thus structured, droplets of medicament liquefied by becoming attaching to the inner wall of the tubular member and the user's saliva are guided by the brim member into the receptacle inside the nebulizer. Thus, the inhalator can be used in a hygienically advantageously way. Since the attachment is of a simple structure, there is no need to increase the number of components to be assembled and the production cost is not unnecessarily increased. Since an air inlet is additionally provided, furthermore, the receptacle does not interfere with the air flow through the inhalator.

It is preferable to form the brim member continuously from one end of the tubular member at the medicament inlet. A brim member thus structured is easier to produce and is more convenient because the liquefied medicament and the patient's saliva can be collected more dependably.

The air inlet may be formed by cutting a portion of the tubular member at the medicament inlet because the air flow inside the tubular member can be stabilized more reliably than if a separate inlet is provided elsewhere. A stabilized air flow through the tubular member makes it easier for the user to breathe in the medicament. Since such a cut can be easily formed, the production process need not be complicated.

A nebulizer according to this invention may be characterized as comprising a main body and an attachment as described above which is detachably attached to the main body. The main body includes a receptacle, a nebulization mechanism for nebulizing a medicament liquid and a medicament outlet for causing a nebulized medicament from the nebulization mechanism to be emitted therethrough.

DETAILED DESCRIPTION OF THE INVENTION

Figure 1:
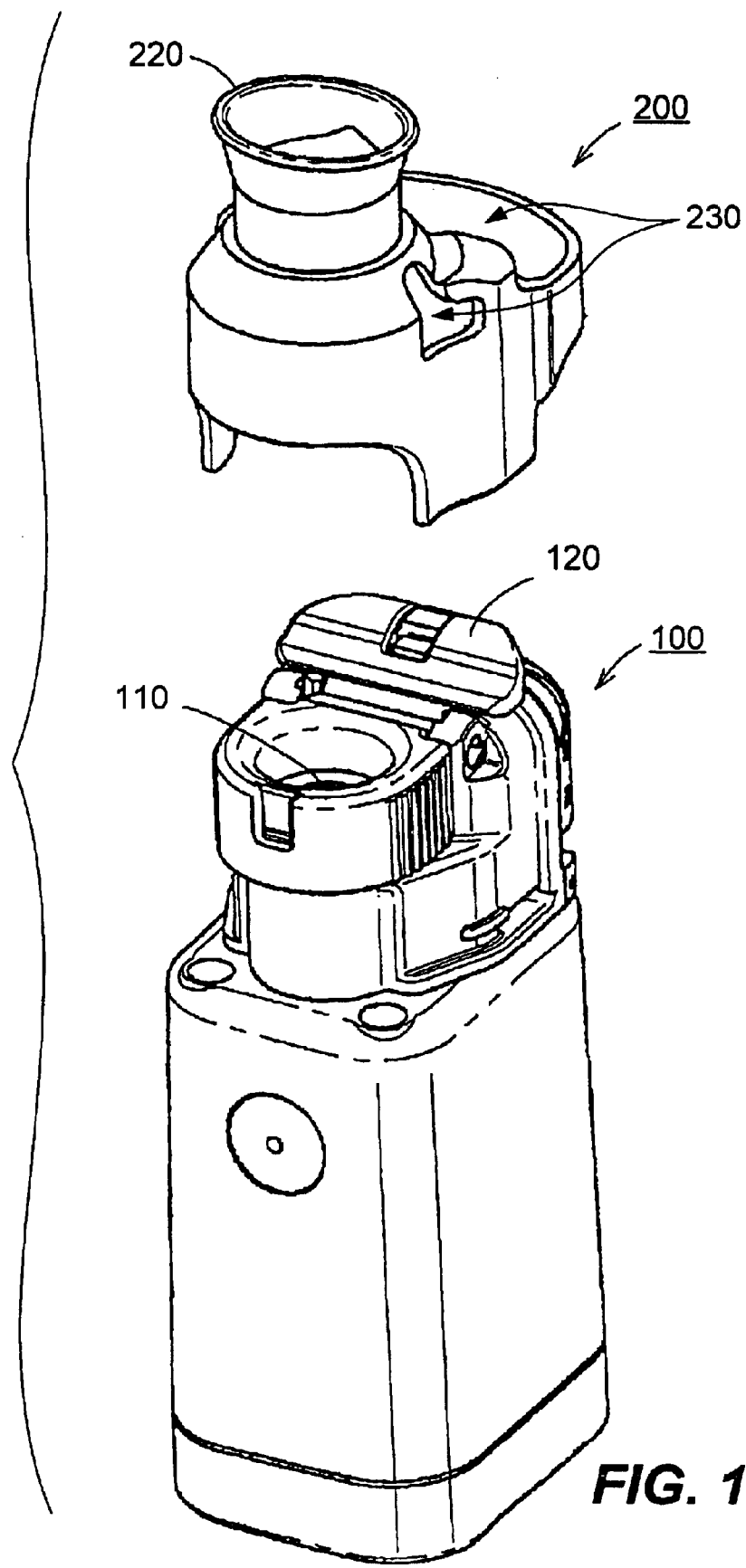
FIG. 1 is an external view of a mouthpiece as an inhalator attachment and a nebulizer of this invention separated from each other.
Figure 2:
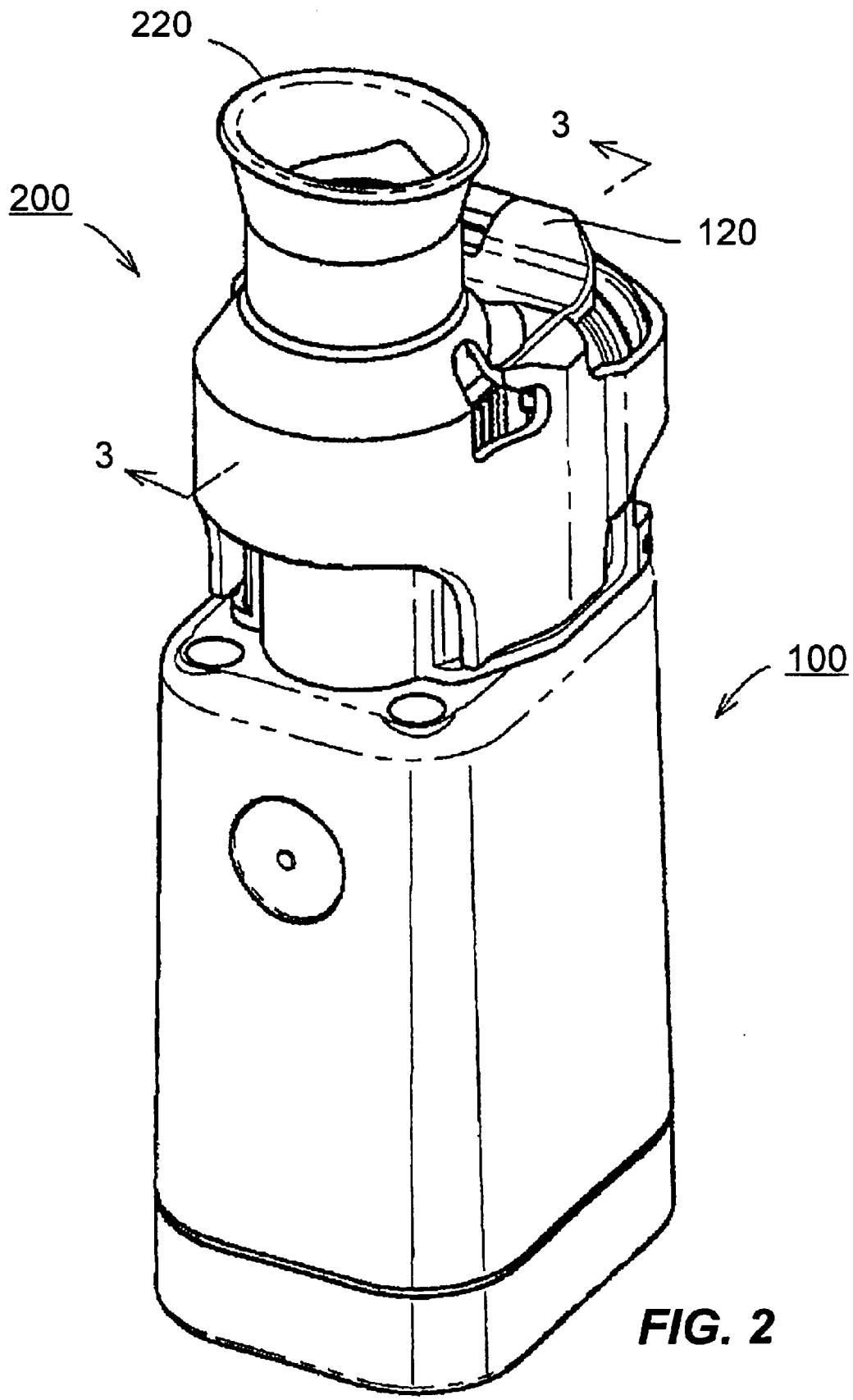
FIG. 2 is an external view of the mouthpiece and the nebulizer of FIG. 1 when they are assembled together.
Figure 3A:
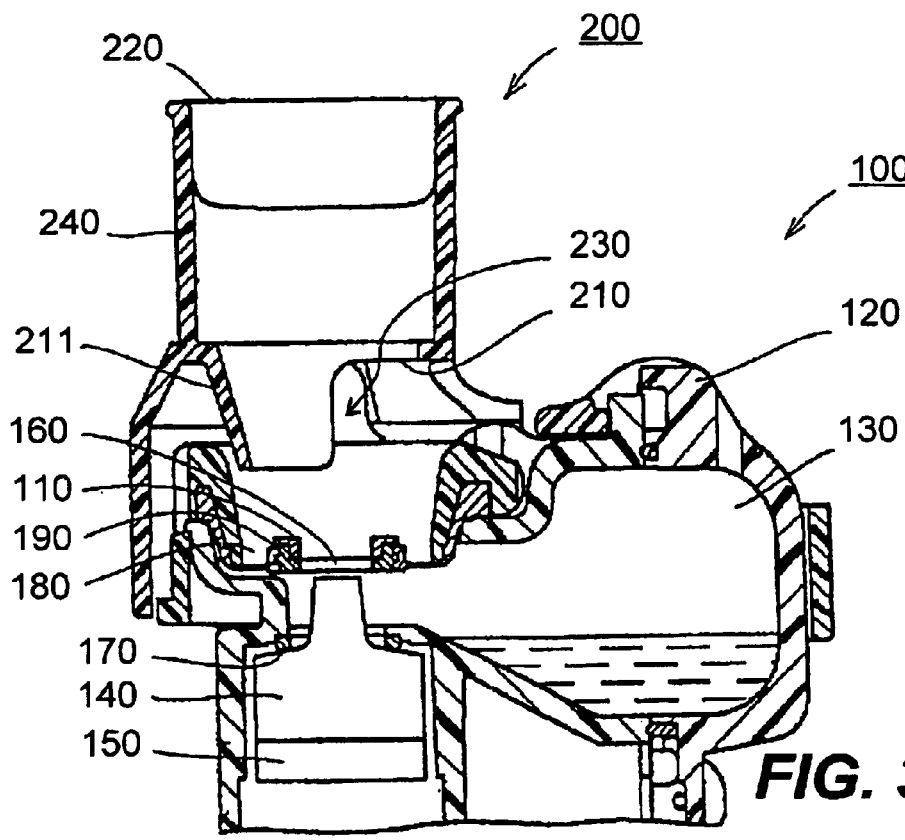
FIG. 3A is a schematic sectional view of the inhalator taken along line 3—3 in FIG. 2

FIG. 1 shows a mouthpiece as an inhalator attachment 200 and a nebulizer 100 of this invention separated from each other and FIG. 2 shows them assembled together. The nebulizer 100 is of the aforementioned type provided with a mesh and using ultrasonic vibration. FIG. 3A is a sectional view for showing the inner structure of the inhalator attachment 200 and the nebulizer 100. The nebulizer 100 has an outlet 110 at the top for emitting nebulized medicament, a medicament storage part 130 for storing a liquid medicament and an opening mechanism 120 which may be used conveniently for washing the interior of the storage part 130. The medicament may be supplied into the storage part 130 through the outlet 110.

Figure 3B:
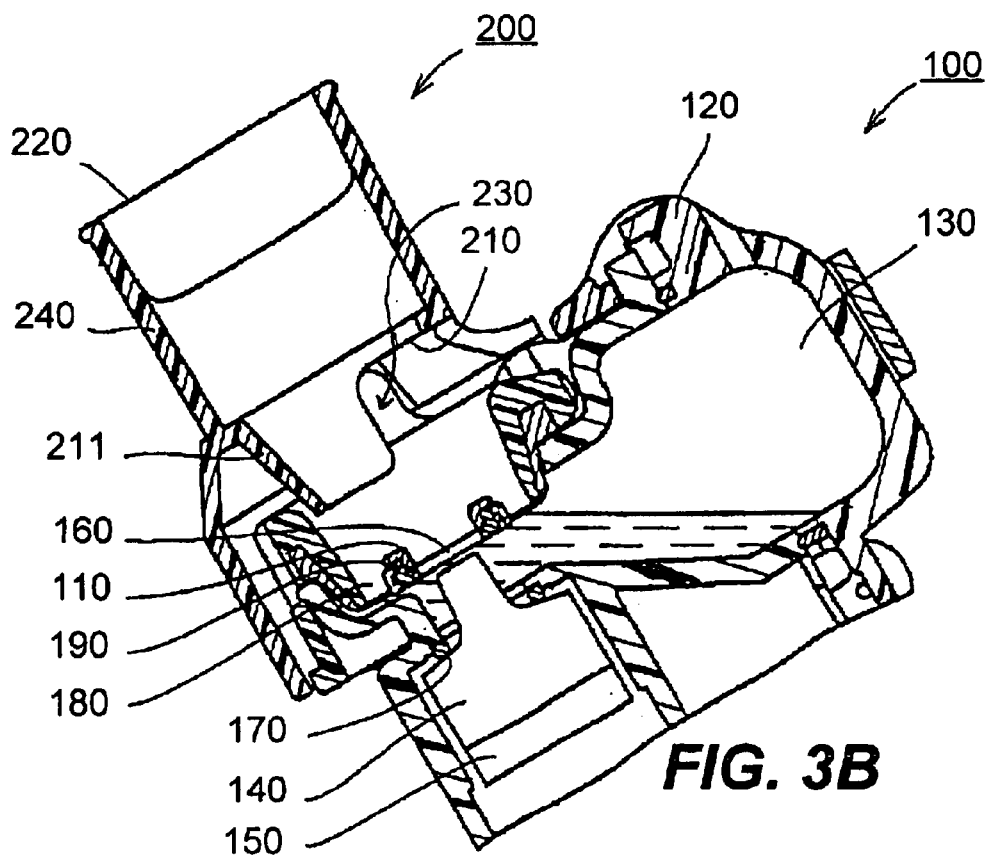
FIG. 3B is another schematic sectional view of the inhalator when it is tilted.

The attachment 200 is unistructurally formed of a resin material in a shape so as to be attachable to the top of the nebulizer 100, including a tubular member 240 through which nebulized medicament emitted from the nebulizer 100 through its outlet 110 will pass. At the top of the attachment 200 is an inhalation opening 220 to be inserted into the patient's mouth. It is not in an airtight manner that the tubular part 240 of the attachment 200 is to be attached to the medicament-emitting outlet 110 of the nebulizer 100, but there are air inlets 230 provided at appropriate positions for introducing air inward. The nebulizer 100 is intended to be hand-held by the patient with the attachment 200 attached in place with its inhalation opening 220 inserted into and held in the mouth. The nebulizer 100 need not be held in an upright position as shown in FIG. 3A but may be tilted somewhat towards the patient as shown in FIG. 3B. Right below the medicament-emitting outlet 110, the nebulizer 100 has its ultrasonic nebulization mechanism including a piezoelectric element 150, a step horn 140 and a mesh 160. The mesh contains many small holes and its bottom surface contacts one end of the step horn 140. The piezoelectric element 150 begins to oscillate when driven by an electric power source, transmitting its vibratory motion to the step horn 140 and thereby causing the medicament liquid to become nebulized over the contact surface between the step horn 140 and the mesh 160. The nebulized medicament is energetically emitted out of the holes in the mesh 160 towards the medicament-emitting outlet 110.

A liquid receptacle 180 is formed around the medicament-emitting outlet 110 for receiving and holding the portion of the nebulized medicament which has become attached to the inner surface of the tubular part 240 and the patient's saliva that is dripping down. A partition plate 190 is provided for preventing these droplets and saliva collected in the receptacle 180 from becoming mixed into the mesh 160 inside the plate 190.

The medicament storage part 130 is next to the nebulization mechanism. A medicament may be supplied into the storage part 130 by opening and closing the outlet 110. As the nebulizer 100 is tilted as shown in FIG. 3B, the medicament inside the storage part 130 can be completely nebulized by the nebulization mechanism. For this purpose, the nebulization mechanism is provided with an O-ring 170 to keep a liquid-tight condition.

As explained above, the attachment 200 comprises a tubular part 240 with a bottom opening (as medicament inlet) 210 which faces the medicament-emitting outlet 110 of the nebulizer 100 when the attachment 200 is attached to the nebulizer 100. A brim part 211 is provided, continuing downward from a portion of the circumference of the bottom opening 210 from the tubular part 240, extending towards the receptacle 180. This brim part 211 serves as a guide to collect the portion of the medicament which has become attached to the inner wall of the tubular part 240 to become droplets of liquid and the patient's saliva without allowing them to spill out and to guide them into the receptacle 180 on the nebulizer 100.

The brim part 211 is formed only partially around the bottom opening 210 of the tubular part 240 such that the tubular part 240 will become closed in an airtight manner. The remaining portion of the circumference of the bottom opening 210, not having the brim part 211 extending therefrom, becomes a portion of the aforementioned air inlet 230. This portion of the air inlet 230 may be formed by cutting open a portion of the bottom opening 210 such that there will always be an air flow through the tubular part 240.

Since the patient frequently tilts the nebulizer 100 in the way shown in FIG. 3B, the brim part 211 is formed halfway around the circumference of the bottom opening 210 on the tilted side, as shown in FIGS. 3A and 3B. Since the brim part 211 and the air inlet 230 are both of a very simple structure, they can be formed in the same production process step when the attachment 200 is produced.

With the nebulizer 100 and the attachment 200 thus structured, the air flow through the tubular part 240 can be maintained while the droplets of medicament and the patient's saliva dripping along the inner wall of the attachment 200 can be prevented from flowing outside. Instead, they are efficiently collected by the brim part 211 because the nebulizer 100 is usually tilted when in use and become led into the receptacle 180. Thus, the nebulizer 100 can be used in a more hygienically desirable way.

Figure 4:
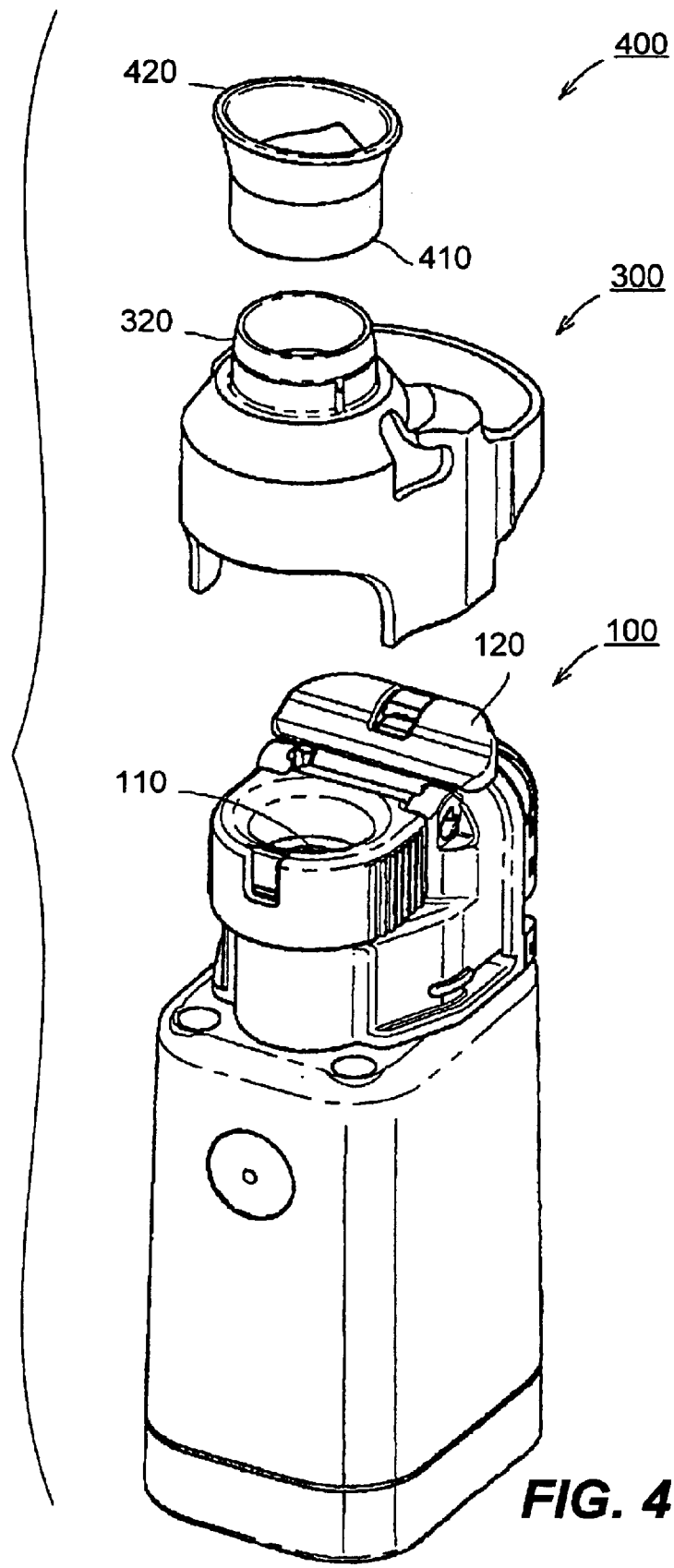
FIG. 4 is an external view of the inhalator of this invention before a mouthpiece and its adaptor are attached.
Figure 5:
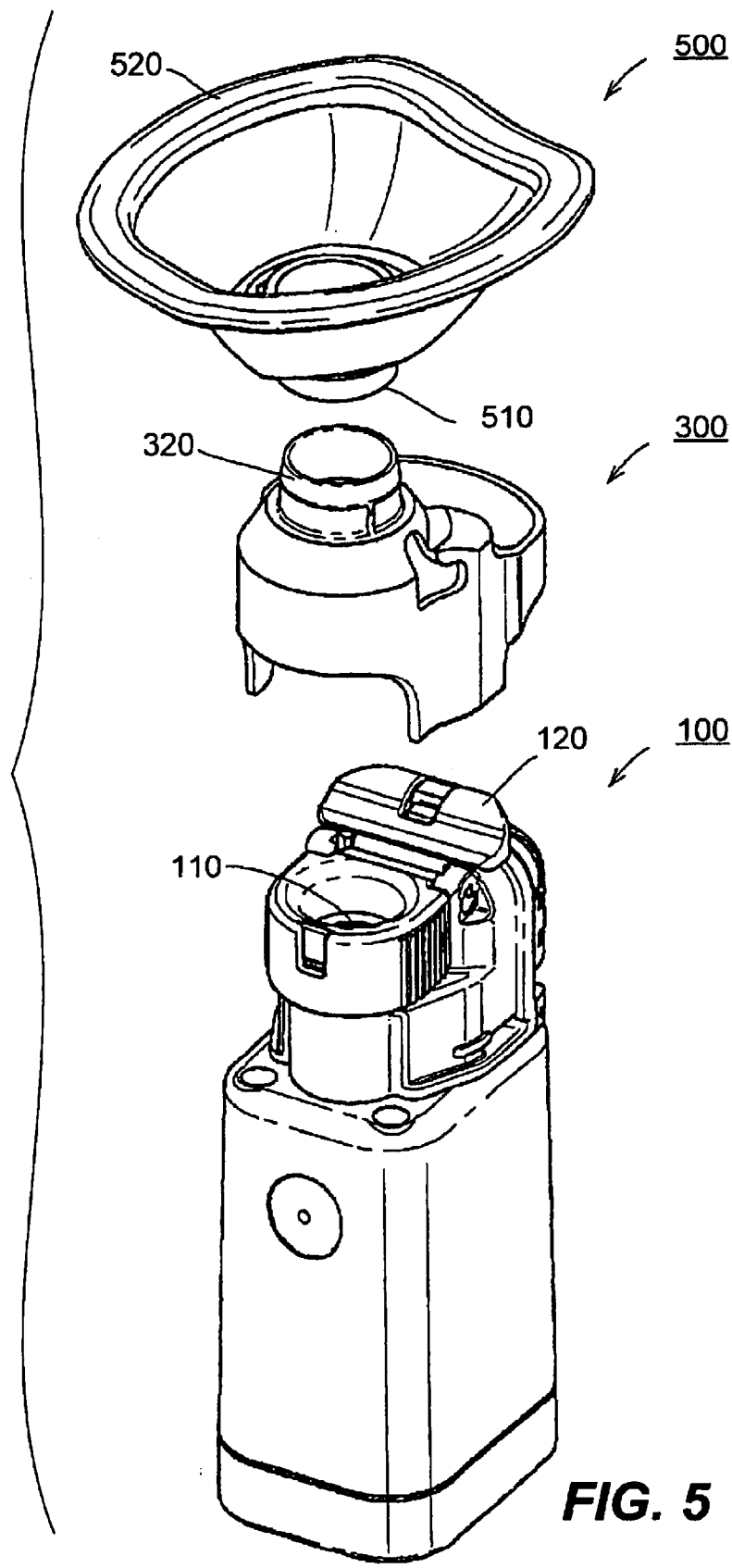
FIG. 5 is an external view of the inhalator of this invention before a mask and its adaptor are attached.

FIG. 4 shows another nebulizer attachment embodying this invention characterized as having the attachment 200 shown in FIG. 1 made separable into a mouthpiece 400 and an adapter 300. FIG. 5 shows still another embodiment characterized as having the mouthpiece 400 of FIG. 4 replaced by a mask 500 with an opening 520. It is to be understood, although not shown, that a brim part such as shown at 211 in FIGS. 3A and 3B is provided to the adapter 300.

Although the invention has been described with reference to a nebulizer using an ultrasonic vibrator with a mesh, this is not intended to limit the scope of the invention. Inhalator attachments of this invention may be used with a nebulizer of any kind. Similarly, although examples have been shown with a brim part formed halfway around the circumference of the bottom opening, neither is this shape of the brim part intended to limit the scope of the invention. The brim may be of any shape as long as it is capable of collecting the liquefied medicament and saliva and introducing them into the liquid receptacle. It must be shaped, however, such that it can be integrally formed when the inhalator attachment is produced by molding and that the flow of air through the attachment is not adversely affected.

In summary, the illustrated examples are to be considered as being demonstrative and not as limiting. Modifications and variations that may be apparent to a person skilled in the art are all intended to be included within the scope of the invention.

What is claimed is:

1. An inhalator attachment to a nebulizer having an receptacle and an outlet for nebulized medicament, said attachment comprising:

a tubular member having a medicament inlet for receiving nebulized medicament from said nebulizer, an inhalation opening which is opposite said medicament inlet and through which a patent inhales said nebulized medicament passed through said tubular member, and an air inlet through which air outside is introduced to be passed through said tubular member; and a brim member for guiding liquid droplets on said tubular member into said receptacle.

2. The inhalator attachment of claim 1 wherein said brim member is formed continuously from one end of said tubular member at said medicament inlet.

3. The inhalator attachment of claim 2 wherein said brim member is formed partially around said medicament inlet.

4. The inhalator attachment of claim 1 wherein said air inlet is formed by providing said tubular member with a cut at said medicament inlet.

5. The inhalator attachment of claim 2 wherein said air inlet is formed by providing said tubular member with a cut at said medicament inlet.

6. A nebulizer comprising:

a main body having a receptacle, a nebulization mechanism for nebulizing a medicament liquid and a medicament outlet for causing a nebulized medicament from said nebulization mechanism to be emitted therethrough, and an attachment which is detachably attachable to said main body, said attachment comprising a tubular member having a medicament inlet for receiving nebulized medicament from said nebulizer, an inhalation opening which is opposite said medicament inlet and through which a patent inhales said nebulized medicament passed through said tubular member, and an air inlet through which air outside is introduced to be passed through said tubular member, and a brim member for guiding liquid droplets on said tubular member into said receptacle.

7. The nebulizer of claim 6 wherein said brim member is formed continuously from one end of said tubular member at said medicament inlet.

8. The nebulizer of claim 7 wherein said brim member is formed partially around said medicament inlet.

9. The nebulizer of claim 6 wherein said air inlet is formed by providing said tubular member with a cut at said medicament inlet.

10. The nebulizer of claim 7 wherein said air inlet is formed by providing said tubular member with a cut at said medicament inlet.

* * * * *